(12) United States Patent
Bain et al.

(10) Patent No.: US 11,598,747 B2
(45) Date of Patent: Mar. 7, 2023

(54) BLOOD PH MEASUREMENT USING ELECTROLYTE SEPARATION LAYER

(71) Applicant: Sentient Technologies, Inc., Los Gatos, CA (US)

(72) Inventors: Harold Mark Bain, Palo Alto, CA (US); Fredrick Quincy Johnson, Pleasanton, CA (US); Henry Roskos, Las Vegas, CA (US)

(73) Assignee: Sentient Technologies, Inc., Los Gatos, CA (US)

( * ) Notice: Subject to any disclaimer, the term of this patent is extended or adjusted under 35 U.S.C. 154(b) by 0 days.

(21) Appl. No.: 15/841,234

(22) Filed: Dec. 13, 2017

(65) Prior Publication Data

US 2019/0178836 A1 Jun. 13, 2019

(51) Int. Cl.
*G01N 27/414* (2006.01)
*G01N 33/84* (2006.01)
*G01N 33/49* (2006.01)

(52) U.S. Cl.
CPC ........... *G01N 27/414* (2013.01); *G01N 33/49* (2013.01); *G01N 33/84* (2013.01)

(58) Field of Classification Search
CPC .. G01N 27/414; G01N 27/4167; G01N 33/49; G01N 33/84
See application file for complete search history.

(56) References Cited

U.S. PATENT DOCUMENTS

| 4,307,195 A | * | 12/1981 | Karasawa | C12Q 1/002 435/182 |
| 8,774,885 B2 | | 7/2014 | Abreu | |
| 2010/0036279 A1 | * | 2/2010 | Rieth | A61B 5/14539 600/551 |

(Continued)

FOREIGN PATENT DOCUMENTS

| EP | 2130045 B1 | 12/2010 |
| EP | 2570803 A1 | 3/2013 |

(Continued)

OTHER PUBLICATIONS

Cellulose acetate defined by Britannica (Year: 2021).*

(Continued)

*Primary Examiner* — Luan V Van
*Assistant Examiner* — Caitlyn Mingyun Sun
(74) *Attorney, Agent, or Firm* — Fish IP Law, LLP

(57) ABSTRACT

A blood pH measurement device comprises a tube through which blood or other ion-containing fluid flows, at least one dry reference electrode, a proton diffusion differentiator, an ion-sensitive field-effect transistor, and a pH meter. The tube can comprise an annular wall with an entry, an exit, and a sensor floor. The dry reference electrode is preferably located within the tube between the entry and the exit and opposite the sensor floor. It is also contemplated that the dry reference electrode is surrounded by a membrane and is, at least partially, associated with the interior surface of the annular wall. The contemplated invention can also include a proton diffusion differentiator, such as an electrolyte sepa- (Continued)

ration layer, connecting the external surface of the sensor floor to an ion-selective field effect transistor (ISFET), wherein the ISFET measures the ion concentration of the blood.

17 Claims, 2 Drawing Sheets

(56) References Cited

U.S. PATENT DOCUMENTS

| | | | | |
|---|---|---|---|---|
| 2012/0143027 | A1* | 6/2012 | Phillips | G01N 27/4145 600/345 |
| 2013/0197333 | A1* | 8/2013 | Petisce | A61B 5/14532 600/347 |
| 2013/0202721 | A1 | 8/2013 | Silver | |
| 2015/0230742 | A1* | 8/2015 | Silver | A61B 5/0031 600/348 |
| 2017/0020408 | A1 | 1/2017 | Rowe et al. | |
| 2017/0059514 | A1* | 3/2017 | Hoffman | G01N 33/5438 |

FOREIGN PATENT DOCUMENTS

| | | | | |
|---|---|---|---|---|
| EP | 2924424 A1 | * | 9/2015 | ......... G01N 27/4165 |
| WO | 2009081291 | | 7/2009 | |
| WO | WO-2011040803 A1 | * | 4/2011 | ......... G01N 27/4148 |

OTHER PUBLICATIONS

Ag/AgCl Reference Electrode (Year: 2021).*
Nafion—Wikipedia (Year: 2022).*
Acetylcellulose _ C1 Oh 1608 - PubChem (Year: 2022).*

* cited by examiner

BLOOD PH MEASUREMENT USING ELECTROLYTE SEPARATION LAYER

FIELD OF THE INVENTION

The field of the invention is blood pH measurement.

BACKGROUND

The following description includes information that may be useful in understanding the present invention. It is not an admission that any of the information provided herein is prior art or relevant to the presently claimed invention, or that any publication specifically or implicitly referenced is prior art.

Blood pH measurement requires separation of H+ ions from other ions present in blood. Conventional blood pH measurement devices work slowly because H+ ions are not quickly separated from other ions using techniques known in the art, such as using a concentration gradient to cause the movement of H+ across a barrier. Some blood pH measurement devices rely on creating an electrical gradient to attract positive H+ ions to a negatively charged electrode through a separation layer. The separation layer forms a barrier between an oxide layer of a gate of the blood pH meter. However, increasing the diffusion speed of H+ towards an oxide layer of the gate also attracts other position ions towards the gate of the blood pH meter. The accumulation of other cations on and within the separation layer alters the gate conductivity, which in turn, causes inaccurate measurements of H+ concentration. In order to take accurate measurements of H+ concentration in the blood stream using this method, the separation layer must be extremely thick compared to conventional separation layers. As a result, the increased diffusion speed of the H+ towards the gate can be rendered ineffective by the increased amount of time required for H+ to diffuse through the thicker separation layer.

Using an electrolyte barrier with $H_2O$ separation in blood pH measurement systems greatly improves over the prior art by increasing the speed of H+ diffusion towards the oxide layer of the gate while maintaining a large separation between the gate and non-H+ positively charged ions, which increases the accuracy of blood pH measurements. Electrolyte barriers with $H_2O$ separation placed between the separation layer and the gate apply external bias that draws H+ ions out of a solution at much greater speeds than concentration gradient or electrode-based systems. Additionally, the increased distance between the oxide layer of the gate and the non-H+ positively charged ions allows the blood pH measurement system to differentiate the concentration of H+ ions from the concentration of all positively charged mobile ions. As a result, blood pH measurement systems employing an electrolyte separation layer are able to produce significantly faster and more accurate blood pH readings.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Thus, there is still a need for a method for accurately measuring the pH of saline solutions using ion concentration.

SUMMARY OF THE INVENTION

The inventive subject matter provides apparatus for increasing the speed and accuracy of blood pH measurements using an electrolyte separation layer.

The inventive subject matter can comprise a tube through which blood flows, a dry reference electrode, a proton diffusion differentiator, an ion-selective field effect transistor, and a pH meter. The tube can comprise an annular wall with an entry, an exit, and a sensor floor. The dry reference electrode is preferably located within the tube between the entry and the exit and opposite the sensor floor. It is also contemplated that the dry reference electrode is surrounded by a membrane (e.g., includes a material that is permeable to protons and allows the dry reference electrode to contact the protons within the fluid without requiring active assistance, for example where active assistance is electrode-assisted transport of the protons from the fluid to the dry reference electrode) and is, at least partially, associated with the interior surface of the annular wall. The contemplated invention can also include a proton diffusion differentiator, such as an electrolyte separation layer, connecting the external surface of the sensor floor to an ion-selective field effect transistor (ISFET), wherein the ISFET measures the ion concentration of the blood. In some embodiments, the ISFET is connected to a part of the annular wall and at least a part of a second membrane.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
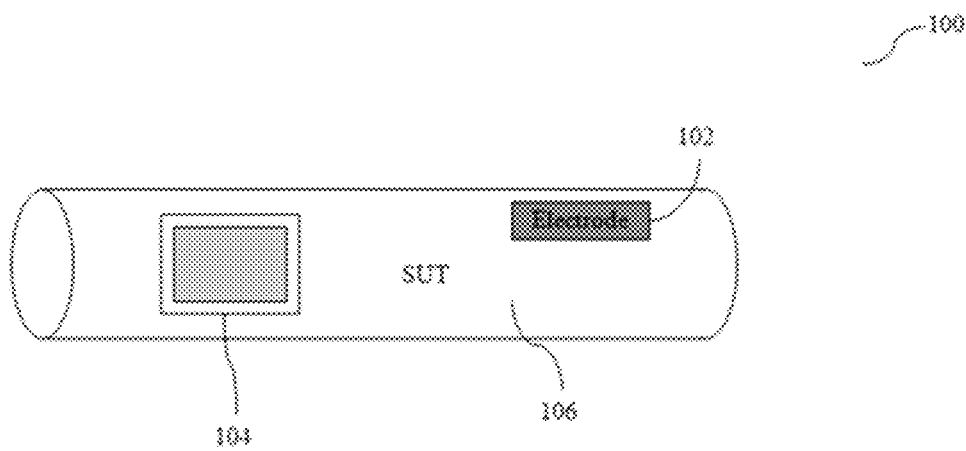
FIG. 1 is a perspective view of a pH measurement system comprising a solution under test ("SUT"), an ion-sensitive field-effect transistor stack, and a reference electrode.

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In FIG. 1, a tube 100 generally includes dry reference electrode 102, an ion-sensitive field-effect transistor ("ISFET") stack 104, and solution under test ("SUT") 106.

Dry reference electrode 102 provides a reference electrical potential. Dry reference electrode 102 is physically separated from SUT 106 by a barrier, which allows dry reference electrode 102 to be submersed in SUT 106. In preferred embodiments, dry reference electrode 102 is coated in sulfonated tetrafluoroethylene-based fluoropolymer-copolymer (e.g., without at least one of silica or zirconium phosphate). Dry reference electrode 102 can also be encapsulated in a solution of Ag or AgCl.

ISFET stack 104 converts the activity of a cation dissolved in a solution into an electrical potential. The electrical potential indicates a degree of bias, which is used to determine an ion concentration. In preferred embodiments, ISFET 104 converts the activity of H+ into an electrical potential to measure H+ ion concentration in the blood.

Figure 2:
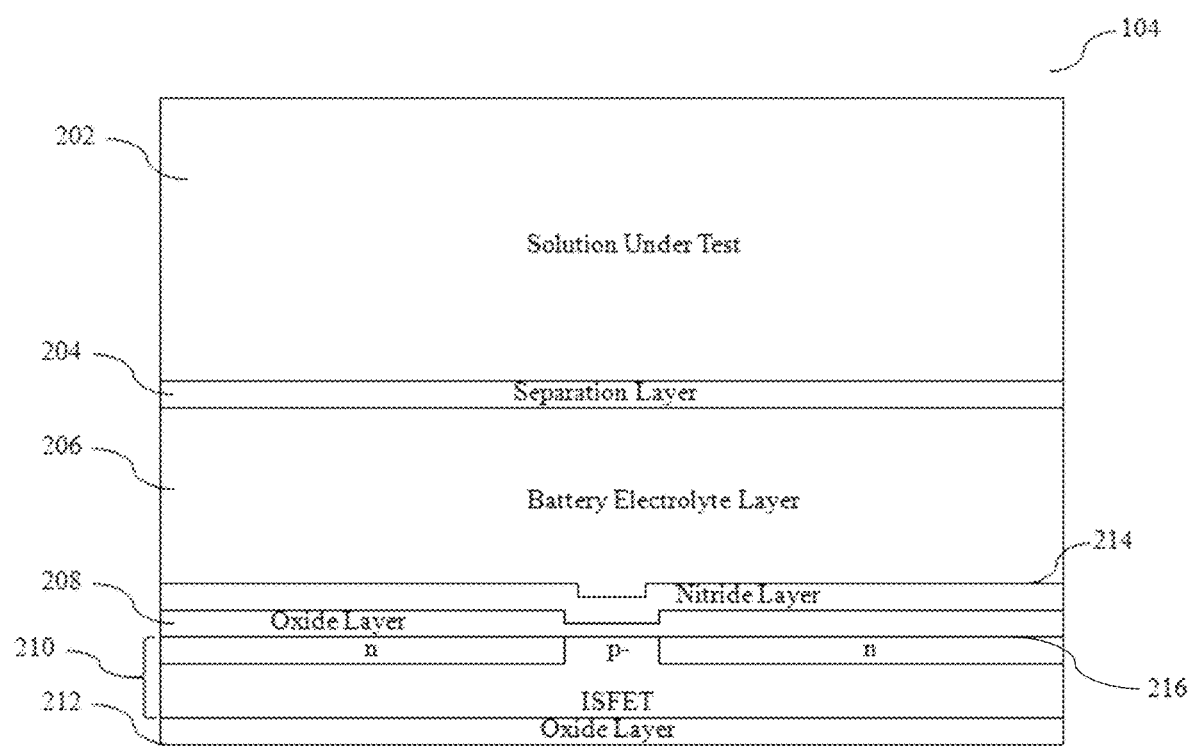
FIG. 2 is a cross-sectional view of a pH measurement device comprising a solution under test ("SUT"), a separation layer, a battery electrolyte layer, a nitride layer, a first oxide layer, an ion-sensitive field-effect transistor, and a second oxide layer.

In FIG. 2, a blood pH measurement system 104 generally includes a solution under test ("SUT") 202, a separation layer 204, battery electrolyte layer 206, nitride layer 214, first oxide layer 208, ion-sensitive field-effect transistor ("ISFET") 210, and second oxide layer 212.

SUT 202 is an ion-containing solution. In a preferred embodiment, SUT 202 is human blood.

Separation layer 204 separates battery electrolyte in the battery electrolyte layer 206 from SUT 202. Separation layer 204 filters contaminants out of SUT 202. Preferably, separation layer 204 comprises an acetate-based material, such as acetyl cellulose. In another preferred embodiment, separation layer 204 is no thicker than 1 mil. It is contemplated that separation layer 204 can comprise any material and any thickness that allows ions to pass from SUT 202 through separation layer 204 to battery electrolyte layer 206.

Battery electrolyte layer 206 acts as an ion filter that allows H+ ions to travel quickly to nitride layer 214. Battery electrolyte layer 206 also allows blood pH measurement system 204 to differentiate between H+ ions and other positively charged mobile ions by 1) selectively filtering H+ ions and 2) increasing the distance of nitride layer 214, first oxide layer 208, and ISFET 210 from separation layer 204 and SUT 202.

In conventional electrical gradient-based ion measurement systems, charged electrodes attract and cause non-H+ ions to collect at an inner surface of separation layer 204 contacting SUT 202 with ISFET 210 abutting or in close proximity to the outer surface of separation layer 204. The close proximity of non-H+ ions to ISFET 210 alters the bias (i.e., conductivity) of gate surface 216 thereby causing inaccurate ion concentration measurements.

In conventional concentration gradient-based systems, H+ ions diffuse through a barrier where the rate of diffusion is largely dependent on a natural concentration gradient and any naturally occurring electrical gradients. Despite being more accurate than electrical gradient-based systems, conventional concentration-gradient based systems are very slow.

Battery electrolyte layer 206 improves over electrical gradient-based systems by increasing the distance between H+ ions and non-H+ ions. Increasing the distance between H+ ions and non-H+ ions diminishes the influence of non-H+ ions on the gate conductivity of ISFET 210, thereby allowing highly accurate ion concentration measurements. In preferred embodiments, battery electrolyte layer 206 is between 30 and 60 mil in thickness.

Battery electrolyte layer 206 also improves over concentration gradient-based systems by increasing the rate of diffusion through a layer, and thereby further separating H+ ions from non-H+ ions. By increasing the rate of diffusion, H+ ions reach nitride layer 214 more quickly to be measured by ISFET 210. Therefore, battery electrolyte layer 206 can increase the accuracy and/or the speed of ion concentration measurements over systems known in the art.

Nitride layer 214 is a thin insulating layer that further separates H+ ions from non-H+ ions.

First oxide layer 208 separates H+ ions from gate surface 216. First oxide layer 208 allows H+ ions to get in close proximity to gate surface 216 without physical contact. The close proximity of H+ ions to gate surface 216 allows gate surface 216 to be biased. Based on the amount of bias caused by the H+ ions, blood pH measurement system 104 can measure an H+ concentration, which can subsequently be used to determine the relative pH of a solution, such as blood.

ISFET 210 converts the activity of a cation dissolved in a solution into an electrical potential. The electrical potential indicates a degree of bias, which is used to determine an ion concentration. In preferred embodiments, ISFET 210 converts the activity of H+ into an electrical potential to measure H+ ion concentration in the blood.

Second oxide layer 212 provides an insulating barrier to ISFET 210 from corrosion and other positively charged ions that can cause unwanted bias in gate surface 216.

Figure 3:
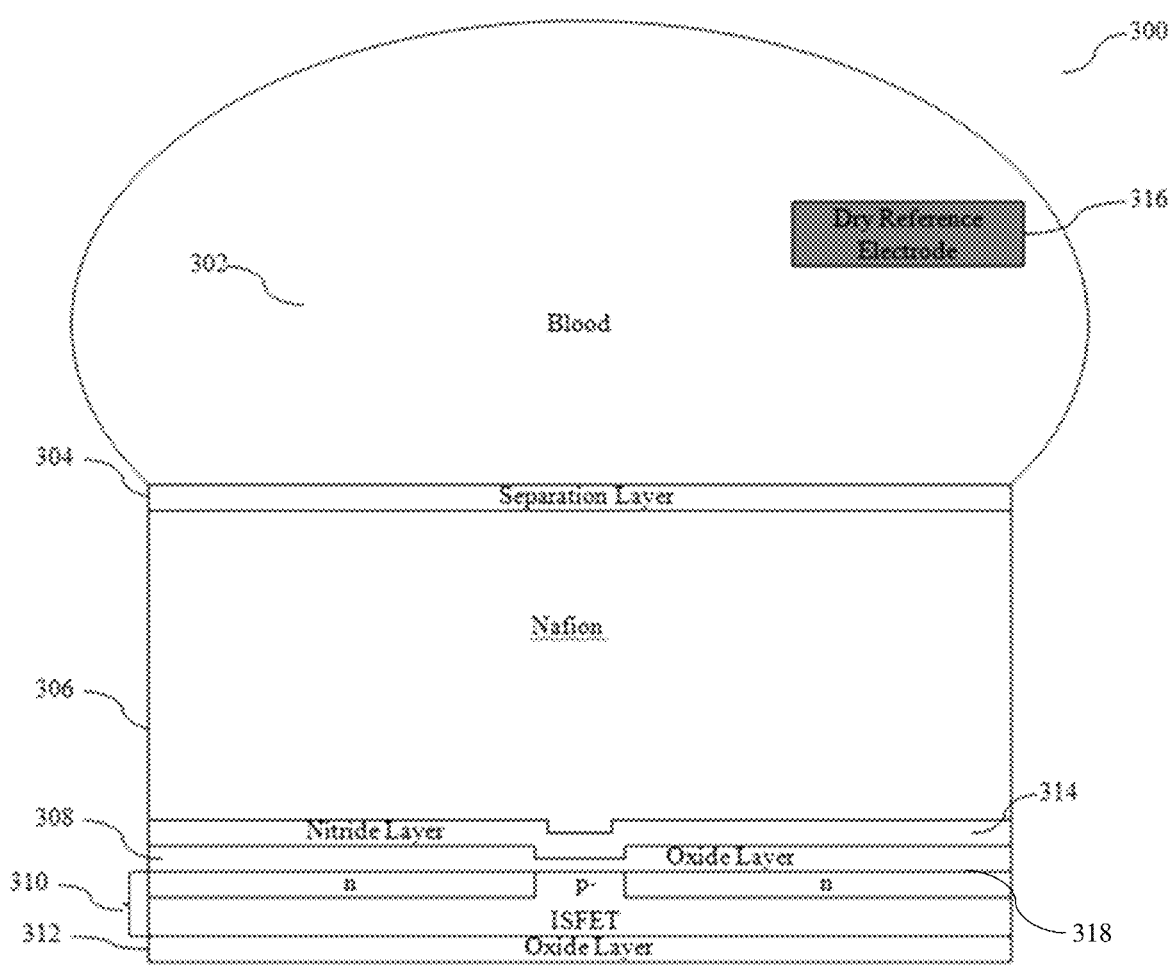
FIG. 3 is a cross-sectional view of a pH measurement device comprising an SUT a separation layer, a battery electrolyte layer, a nitride layer, a first oxide layer, an ion-sensitive field-effect transistor, a second oxide layer, and a reference electrode within the SUT.

In FIG. 3, a blood pH measurement system 300 generally includes blood 302, a acetyl cellulose layer 304, sulfonated tetrafluoroethylene based fluoropolymer-copolymer ("nafion") layer 306, first oxide layer 308, ion-sensitive field-effect transistor ("ISFET") 310, second oxide layer 312, gate surface 318, and reference electrode 316. In some embodiments, blood pH measurement system 300 also comprises a nitride layer.

Blood 302 is preferably human blood, and can alternatively be any ion-containing solution.

Acetyl cellulose layer 304 separates nafion in nafion layer 306 from blood 302. Acetyl cellulose layer 304 filters contaminants, such as blood cells, proteins, and fats, out of blood 302. In another aspect of preferred embodiments, acetyl cellulose layer 304 is no thicker than 1 mil.

Nafion layer 306 is an ion filter that allows H+ ions to travel quickly to first oxide layer 308. Nafion is a sulfonated tetrafluoroethylene based fluoropolymer-copolymer discovered in the late 1960s by Walther Grot of DuPont. Nafion is a class of synthetic polymers with ionic properties, (i.e., ionomers), which are biocompatible with the human body. Nafion layer 306 also allows blood pH measurement system 300 to differentiate between H+ ions and other positively charged mobile ions by 1) selectively filtering H+ ions and 2) increasing the distance of nitride layer 314, first oxide layer 308, and ISFET 310 from separation layer 304 and blood 302.

In conventional electrical gradient-based ion measurement systems, charged electrodes attract and cause non-H+ ions to collect at an inner surface of separation layer 304, which is contacting blood 302, with ISFET 310 abutting or in close proximity to the outer surface of separation layer 304. The close proximity of non-H+ ions to ISFET 310 alters the bias (i.e., conductivity) of gate surface 318 thereby causing inaccurate ion concentration measurements.

In conventional concentration gradient-based systems, H+ ions diffuse through a barrier where the rate of diffusion is largely dependent on a natural concentration gradient and any naturally occurring electrical gradients. Despite being more accurate than electrical gradient-based systems, conventional concentration-gradient based systems are very slow.

Nafion layer 306 improves over electrical gradient-based systems by increasing the distance between H+ ions and non-H+ ions. In preferred embodiments, nafion layer 306 is between 30-70 mil in thickness. Increasing the distance between H+ ions and non-H+ ions diminishes the influence of non-H+ ions on the gate conductivity of ISFET 310 thereby allowing highly accurate ion concentration measurements. Nafion layer 306 also improves over concentration gradient-based systems increasing the rate of diffusion through a layer further separating H+ ions from non-H+ ions. By increasing the rate of diffusion, H+ ions reach first oxide layer 308 more quickly to be measured by ISFET 310. Therefore, nafion layer 306 simultaneously increases the accuracy and the speed of ion concentration measurements over systems known in the art.

First oxide layer 308 separates H+ ions from gate surface 318, but still allows H+ ions to get in close proximity to gate surface 318 without physical contact. The close proximity of H+ ions to gate surface 318 allows gate surface 318 to be biased. Based on the amount of bias caused by the H+ ions, blood pH measurement system 300 can measure an H+ concentration, which can subsequently be used to determine the relative pH of a solution, such as blood.

ISFET 310 converts the activity of a specific ion dissolved in a solution into an electrical potential. The electrical potential indicates a degree of bias, which is used to determine an ion concentration. In the embodiment depicted in FIG. 3, ISFET 310 converts the activity of H+ into an electrical potential to measure H+ ion concentration in the blood.

Dry reference electrode 316 provides a reference electrical potential. Dry reference electrode 316 is physically separated from blood 302 by a barrier, which allows dry reference electrode 316 to be submersed in blood 302. In preferred embodiments, dry reference electrode 316 is coated in sulfonated tetrafluoroethylene-based fluoropolymer-copolymer. Dry reference electrode 316 can also be encapsulated in a solution of Ag or AgCl.

Second oxide layer 312 provides an insulating barrier to ISFET 310 from corrosion and other positively charged ions that can cause unwanted bias in gate surface 318.

Nitride layer 314 is a thin insulating layer that further separates H+ ions from non-H+ ions. In preferred embodiments, blood pH measurement system 300 does not comprise nitride layer 314 because battery electrolyte layer 306 selectively filters H+ ions from blood 302.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A device for directly measuring a pH of a fluid, comprising:
    a tube having an annular wall that defines a lumen;
    a dry reference electrode in the tube and fluidly separated from the fluid by a barrier;
    an ion-selective field effect transistor (ISFET) stack in the tube and fluidly separated from the fluid by a layer, comprising:
        an electrolyte separation layer disposed between the layer and the ISFET and having the structural quality of selectively filtering H+ ions over other cations from the fluid to the ISFET, wherein the electrolyte separation layer does not have a direct interface with the fluid;
        a nitride layer and a first oxide layer disposed between the electrolyte separation layer and the ISFET; and
        a second oxide layer disposed on a surface of the ISFET opposite the first oxide layer;
    wherein a signal from the dry reference electrode is correlated with a H+ ion concentration signal from the ISFET to determine the pH of the fluid.

2. The device of claim 1, wherein the electrolyte separation layer comprises a sulfonated tetrafluoroethylene-based fluoropolymer-copolymer.

3. The device of claim 2, wherein the sulfonated tetrafluoroethylene-based fluoropolymer-copolymer does not comprise at least one of silica or zirconium phosphate.

4. The device of claim 3, wherein the layer is no more than 1 mm thick.

5. The device of claim 4, wherein the barrier encapsulates a solution comprising Ag or AgCl.

6. The device of claim 1, wherein the layer comprises acetyl cellulose.

7. The device of claim 1, wherein the dry reference electrode is at least one of within, contacting, or embedded in the interior surface of the annular wall.

8. The device of claim 1, wherein the ISFET is connected to a part of the annular wall and at least a part of the layer.

9. The device of claim 1, wherein the barrier comprises a material having the structural quality of permeability to H+ ions and allowing the dry reference electrode to contact the H+ ions within the fluid without requiring active assistance.

10. The device of claim 9, wherein the active assistance is electrode-assisted transport of the H+ ions from the fluid to the dry reference electrode.

11. The device of claim 1, wherein the ISFET (i) measures a H+ ion density of the fluid and (ii) is coupled to the tube, and (iii) H+ ions are selectively drawn over other cations from the fluid, through the electrolyte separation layer, to the ISFET.

12. The device of claim 1, wherein the nitride layer is separate from the first oxide layer.

13. The device of claim 1, wherein the nitride layer interfaces with the electrolyte separation layer.

14. The device of claim 1, wherein the first oxide layer interfaces with the ISFET.

15. The device of claim 1, wherein the nitride layer interfaces with the first oxide layer.

16. The device of claim 1, wherein the nitride layer is between the first oxide layer and the electrolyte separation layer.

17. The device of claim 1, wherein the first oxide layer is between the nitride layer and the ISFET.

* * * * *